US005894351A

United States Patent [19]
Colvin, Jr.

[11] Patent Number: 5,894,351
[45] Date of Patent: Apr. 13, 1999

[54] FLUORESCENCE SENSING DEVICE

[76] Inventor: Arthur E. Colvin, Jr., 12321 Middlebrook Rd., Germantown, Md. 20874

[21] Appl. No.: 08/855,234

[22] Filed: May 13, 1997

[51] Int. Cl.$^6$ ........................................ G01N 21/25
[52] U.S. Cl. ........................................ 356/417; 422/82.07
[58] Field of Search ........................ 356/417, 416; 250/458.1, 365; 422/82.07

[56] References Cited

U.S. PATENT DOCUMENTS 5,517,313  5/1996  Colvin, Jr. ........................... 356/417
5,591,407  1/1997  Groger et al. .

FOREIGN PATENT DOCUMENTS 725269  8/1996  European Pat. Off. .

OTHER PUBLICATIONS

Colvin, Jr., A.E., et al., "A Novel Solid–State Oxygen Sensor," *Johns Hopkins APL Technical Digest*, vol. 17, No. 4, pp. 377–385 (1996).

*Primary Examiner*—Robert Kim
*Assistant Examiner*—Tu T. Nguyen
*Attorney, Agent, or Firm*—Rothwell, Figg, Ernst & Kurz

[57] ABSTRACT

A fluorescence sensing device for determining the presence or concentration of an analyte in a liquid or gaseous medium is constructed of a light-emitting diode having a hole generally perpendicular to the P-N junction, such that light is emitted from said junction into said hole. The hole is filled with a fluorescent matrix which is permeable to analyte and which contains fluorescent indicator molecules whose fluorescence is attenuated or enhanced by the presence of analyte. A photodetector is positioned at one end of the hole, such that fluorescent light received from the fluorescent indicator molecules if converted to an electrical signal that may be correlated to the presence or concentration of analyte in a gaseous or liquid medium in contact with the fluorescent matrix.

21 Claims, 6 Drawing Sheets

(PRIOR ART) FIG. 1
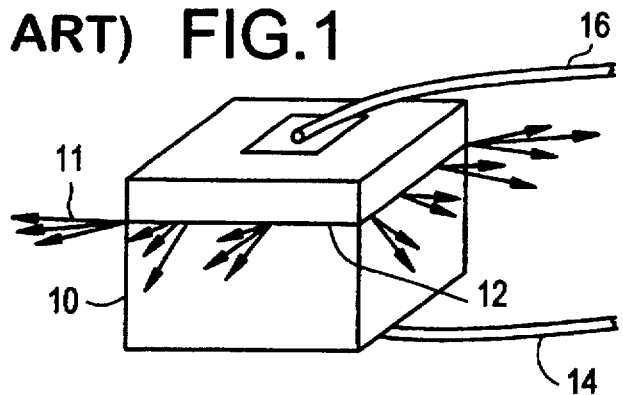
FIG. 2
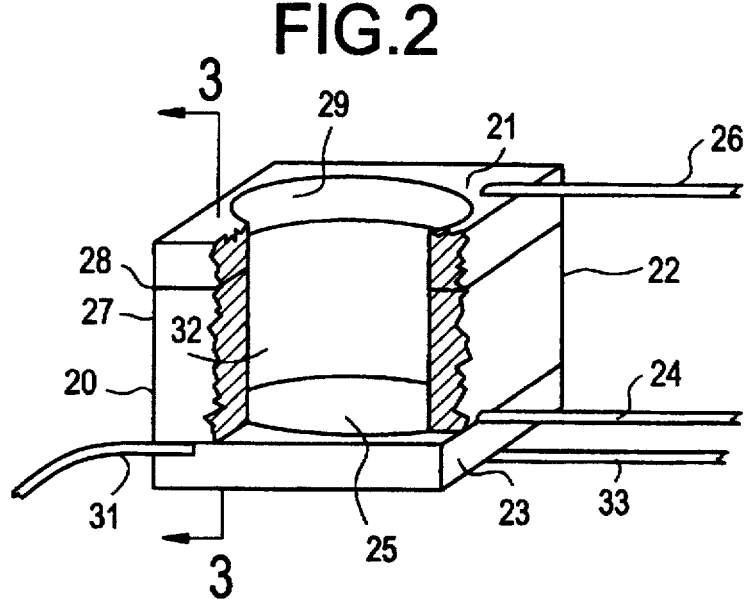
FIG. 3
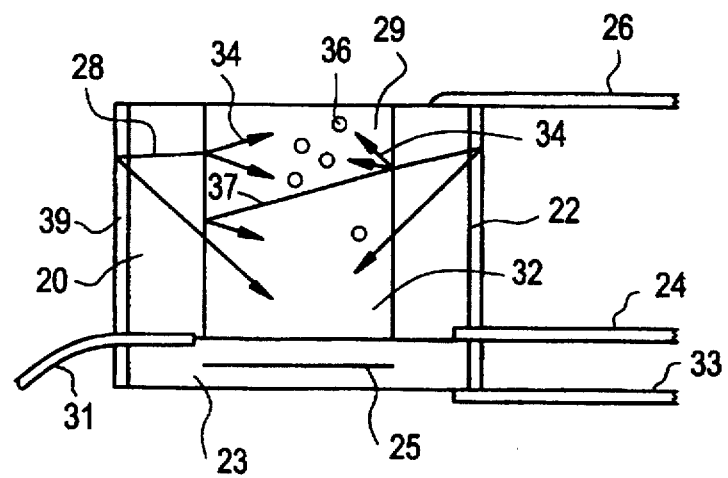

FLUORESCENCE SENSING DEVICE

BACKGROUND OF THE INVENTION

1. Field of Invention

This invention relates to an electro-optical sensing device for detecting the presence or concentration of an analyte in a liquid or gaseous medium. More particularly, the invention relates to a fluorescence sensing device which is characterized by an extraordinarily compact size, fast response times and high signal-to-noise ratios.

2. Background Art

U.S. Pat. No. 5,517,313, the disclosure of which is incorporated herein by reference, describes a fluorescence sensing device comprising a layered array of a fluorescent indicator molecule-containing material, a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source.

The fluorescence of the indicator molecules employed in the device described in U.S. Pat. No. 5,517,313 is modulated, i.e., attenuated or enhanced by the local presence of the analyte. For example, the orange-red fluorescence of the complex, tris(4,7-diphenyl-1,10-phenanthroline) ruthenium(II) perchlorate is quenched by the local presence of oxygen. This complex can, therefore, advantageously be used as the indicator molecule of an oxygen sensor. Similarly, other indicator molecules whose fluorescence is affected by specific analytes are known.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator molecules. The light source, indicator molecule-containing material, high-pass filter and photodetector are configured such that fluorescence emitted by the indicator molecules impacts the photodetector, generating an electrical signal which is indicative of the concentration of the analyte in the surrounding medium.

While the sensing device described in U.S. Pat. No. 5,517,313 represents a marked improvement over prior art devices, there remains a need for sensors that are even more compact, less expensive and which have superior sensing characteristics to those described therein. Thus, it is an object of the present invention to provide an improvement to the sensing devices described in the aforementioned patent.

BRIEF DESCRIPTION OF THE DRAWINGS

The invention will be illustrated by reference to the accompanying drawings in which:

FIG. 1 is a perspective view of a conventional light-emitting diode.

FIG. 2 is a perspective view illustrating a sensing device in accordance with the present invention;

FIG. 3 is a cross-sectional view of the sensing device of FIG. 2, taken along lines 3—3 of FIG. 2;

SUMMARY OF THE INVENTION

Figure 4:
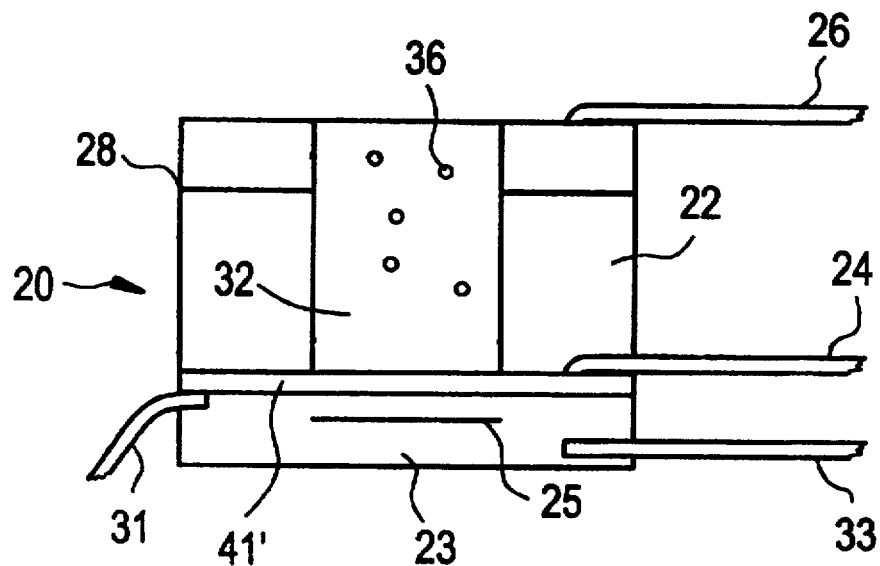
FIG. 4 is a cross-sectional view of an alternative embodiment of a sensing device in accordance with the present invention.

In accordance with the present invention, a fluorescence sensing device for determining the presence or concentration of an analyte in a liquid or gaseous medium comprises (a) a light-emitting P-N junction (referred to hereinafter as a light-emitting diode ("LED")), said LED having a hole in a direction generally perpendicular to the P-N junction plane, said hole configured such that, upon application of an electrical potential across the junction, light is emitted from said junction into said hole;

(b) an analyte-permeable fluorescent matrix contained within at least part of said hole, said fluorescent matrix containing fluorescent indicator molecules whose fluorescence is attenuated or enhanced by the presence of an analyte in said fluorescent matrix; said LED and fluorescent indicator molecules being selected such that the wavelength emitted by the LED excites fluorescence in the indicator molecules; and (c) a photodetector at one end of said hole which generates an electrical signal responsive to fluorescent light emitted by said fluorescent indicator molecules.

DETAILED DESCRIPTION OF THE INVENTION

A conventional LED is illustrated in FIG. 1. LED 10 consists of a layer of N-type semiconductor and a layer of P-type semiconductor, which at the P-N interface 12 form a light-emitting junction. When an electrical potential is applied across P-N junction 12, e.g., via electrical leads 14 and 16, light rays 11 are emitted from the junction in approximately the same plane as the junction. As illustrated in U.S. Pat. No. 5,517,313, this edge-emitting characteristic of LED has been used advantageously for directing light transversely through a layer of fluorescent matrix in an electro-optical sensor.

LEDs are conventionally manufactured by first preparing a bilayer semiconductor wafer using known infusion doping techniques and then cutting or dicing the resulting wafer into chips of appropriate size. LEDs typically are quite small, measuring on the order of 200–300 microns on an edge.

In accordance with the present invention, it has been discovered that, surprisingly, a hole or cavity can be cut into an LED chip without destroying or substantially damaging the functionality of the light-emitting P-N junction. Thus, upon application of an electrical potential across the junction, light is emitted from the junction into the hole or cavity. FIG. 2 illustrates a device of the present invention in perspective, partially cut-away view. Sensor 20 includes an LED 22 having input leads 24 and 26 for applying an electrical potential across P-N junction 28. The LED has a hole 29 cut through it in an orientation generally perpendicular to P-N junction 28.

As illustrated in FIG. 3, a polymer matrix 32 which contains fluorescent indicator molecules whose fluorescence is attenuated or enhanced by the presence of analyte is placed in hole 29. The fluorescent matrix is permeable to analyte such that analyte present in a gaseous or liquid medium exposed to the open end of hole 29 can diffuse into and out of fluorescent matrix 32. The hole 29 may be filled to a level such that the light rays are emitted into the fluorescent matrix 32. For example, hole 29 may be filled completely (i.e. parallel with the top surface of the LED). Hole 29 also may be filled to a level sufficient to cover P-N junction 28.

In one embodiment of the present invention, a photodetector 23 may be positioned at one end of LED 22 with a photosensitive area 25 adjacent hole 29. The photodetector may be a conventional solid state photoelectric device resulting from the interface of two semiconductors. In a preferred embodiment, the light sensitive area 25 corresponds to the area adjacent hole 29. This light sensitive area may be produced by conventional photomasking techniques well known in the art. The electrical signal generated by photodetector 23 is transmitted via electrical leads 33 and 31 to appropriate amplification and measuring circuitry (not shown).

The operation of sensor 20 is illustrated in the cross-sectional view of FIG. 3. Upon application of an electrical potential across P-N junction 28 via leads 24 and 26, light rays 34 are emitted into fluorescent matrix 32 which is contained in hole 29. When the light rays impact a fluorescent indicator molecule 36, the molecule fluoresces with an intensity that is dependent upon the concentration of analyte in fluorescent matrix 32. A portion of the fluorescent light is directed downward toward photodetector 23 and impacts light sensitive area 25. Photodetector 23 and light sensitive area 25 generate an electrical signal that is transmitted by leads 33 and 31.

As illustrated in FIG. 3, light emitted from P-N junction 28 into fluorescent matrix 32 is effectively trapped within the device through internal reflectance, thereby improving the overall efficiency of the device. For example, light ray 37 which is not absorbed on a first pass through fluorescent matrix 32 may be reflected from the wall of hole 29 back into the fluorescent matrix where it has another opportunity to impact a fluorescent indicator molecule.

The efficiency of the device may be further enhanced by coating the walls of LED 22 with a reflective, non-conductive material 39. For example, a latex material may be used to coat the walls of LED 22. Thus, light that would otherwise be transmitted out of the device is reflected back through the walls of LED 22 into fluorescence matrix 32.

Hole 29 may be formed in LED 22 by any convenient technique. It has been found that the hole may be machined into LED 22 by means of an excimer laser, preferably one that emits light at a wavelength of approximately 248 nanometers. The excimer laser also may use a wavelength of approximately 193 nanometers, at lower efficiency. The X, Y coordinates of the laser beam are controlled by an aperture, and the depth of the hole 29 is controlled by the number of pulses. The dimensions of hole 29 may vary depending upon the applications to which sensor 20 are to be put. Hole 29 may pass completely through LED 22. Alternatively, a wall or layer of semiconductor material may remain at the end of the hole adjacent the photodetector, provided that it is sufficiently transparent to the light emitted by fluorescent indicator molecules 36. A shallow hole may be suitable so long as the hole passes through the P-N junction. Hole 29 may be any desired shape, and conveniently is cylindrical in shape. The diameter of hole 29 advantageously ranges from about 10 to 300 microns, preferably from about 20 to about 200 microns, and most preferably from about 100 to about 150 microns.

Analyte-permeable fluorescent matrix 32 is preferably a polymer matrix having fluorescent indicator molecules dispersed therein. Advantageously, the polymer is one which can be cast in hole 29, deposited there by evaporation or polymerized from monomers or oligomers in situ. The polymer used in the matrix should be optically transmissive at the wavelength of excitation and emission of the indicator molecules.

A variety of polymers may be used for the preparation of fluorescent matrix 32. The polymer system that has been found useful for preparing an oxygen sensor employs silicone polymer RTV118, available from General Electric Company, Pittsfield, Mass., U.S.A. This polymer may be dissolved in a 1:1 to 1:6 petroleum, ether/chloroform mixture, the fluorescence indicator ruthenium complex referred to above blended into the polymers solution at a concentration of from about 0.1 to about 1 mM, and the resulting mixture placed in hole 29. Evaporation of the solvents results in the deposition of a fluorescent matrix 32 within hole 29.

In one embodiment of the present invention, electrical lead may be attached to the top of semiconductor material forming the LED 22 and electrical lead 24 is connected to the bottom of the LED 22, as illustrated by FIGS. 2-4. As clearly illustrated in FIG. 4a, electrical leads 31 and 33 preferably are attached to the top and bottom respectively of photodetector 23. In a preferred embodiment electrical leads 24 and 31 may be imbedded in an epoxy material which joins LED 22 to photodetector 23.

In an alternative embodiment, the lower surface of LED 22 is in electrical contact with the upper surface of photodetector 23 such that a common electrical contact may be employed (not shown). To facilitate this electrical contact, an electrically conductive adhesive may be used for joining photodetector 23 and LED 22.

Figure 4A:
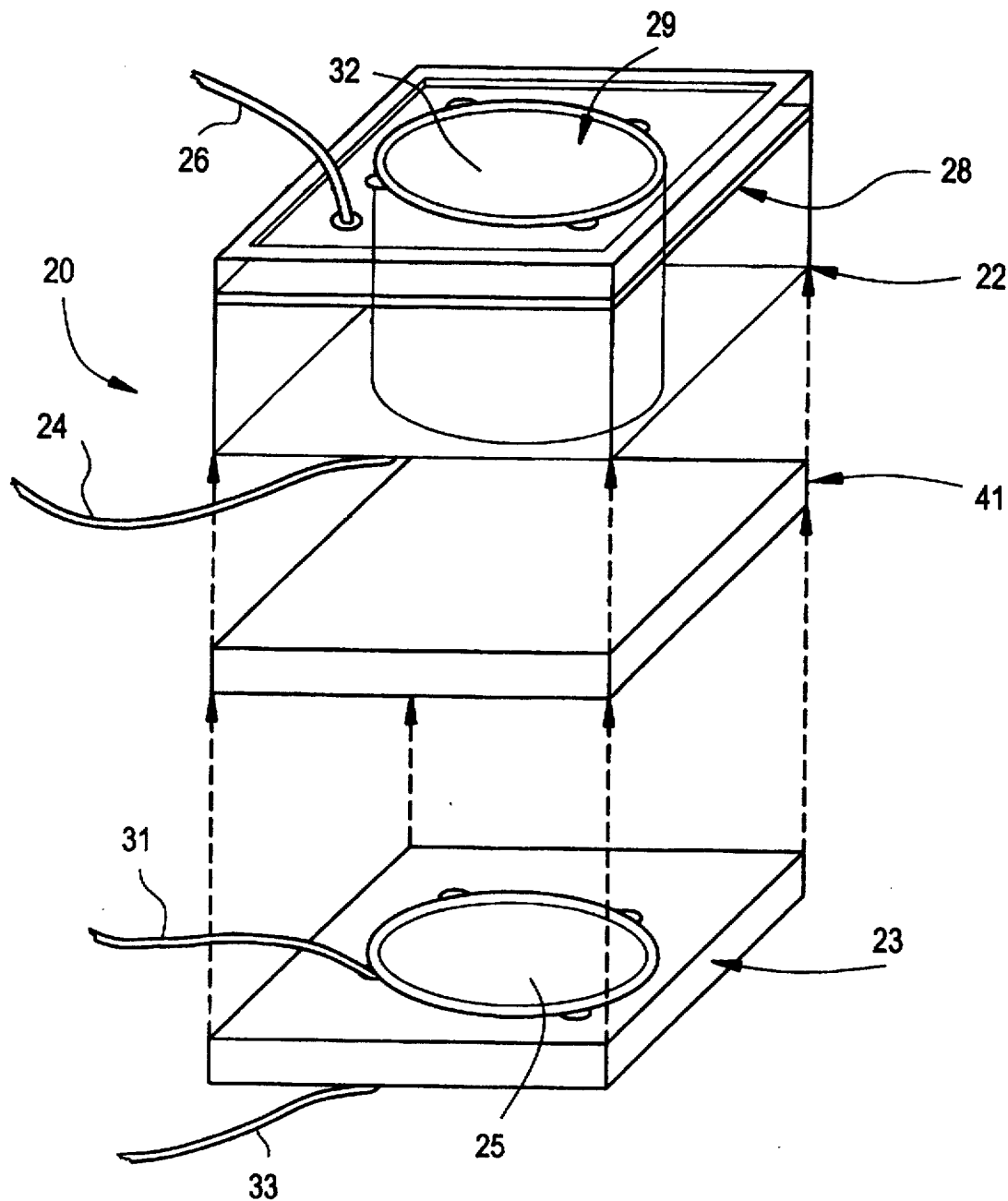
FIG. 4a is an exploded view of the sensing device of FIG. 4.

Because of the physical configuration of sensor 20, very little of the incident light emitted from junction 28 reaches photodetector 23. Nevertheless, small amounts of such light may reach the photodetector through internal reflectance. In addition, ambient light passing through hole 29 may reach photodetector 23. As illustrated in FIGS. 4, an optical cut-off filter 41 may be interposed between fluorescent matrix 32 and photodetector 23. Filter 41 is designed to transmit fluorescent light emitted from fluorescent indicator molecules 36 while filtering out incident light emitted by LED 22 as well as significant portions of ambient light that would otherwise reach photodetector 23. Photodetector 23, filter 41 and LED 22 may be physically joined by means of an adhesive. FIG. 4a illustrates an exploded view of the sensor of FIG. 4.

In one embodiment, the optical filter 41 is coated onto the photodetector 23. Suitable optical filter coating may be obtained from Optical Coating Laboratory, Inc., Santa Rosa, Calif., U.S.A., and applied by conventional methods. See U.S. Pat. No. 5,200,855. In another embodiment, the optical filter may be a colored epoxy which may be used to embed electrical led 24 which is connected to the LED 22. For example, a suitable colored epoxy may be obtained from CVI Laser, Corp., Albuquerque, N. Mex.

Figure 5:
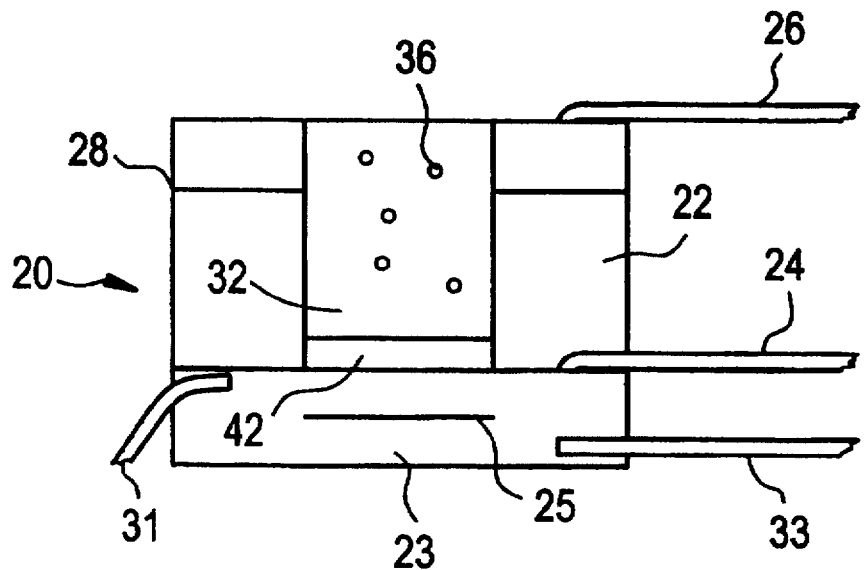
FIG. 5 is a cross-sectional view of another alternative embodiment of a sensing device in accordance with the present invention.

In yet another embodiment, an optical filter 42 may be placed in the hole 29 between the photodetector 23, and the fluorescent matrix 32, as illustrated in FIG. 5. A suitable optical filter may be an epoxy-type filter such as is available from CVI Laser, Corp., Albuquerque, N. Mex.

Figure 6:
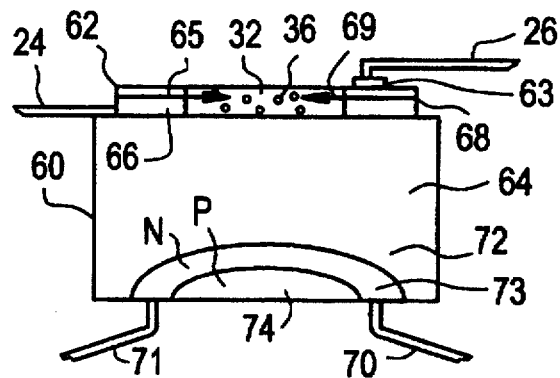
FIG. 6 is a cross-sectional view of another alternative embodiment of a sensing device in accordance with the present invention.
Figure 7:
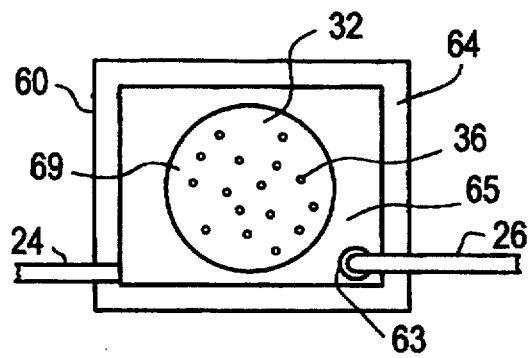
FIG. 7 is a top view of the sensing device of FIG. 6.

FIGS. 6 and 7 illustrate an electro-optical sensing device 60 in accordance with another embodiment of the present invention. Sensor 60 includes an LED 62 supported by a substrate 64. LED 62 preferably is formed by depositing a first semiconductor layer 66 (such as a GaN n-type material) on the top of substrate 64, and then depositing a second semiconductor layer 65 (such as a GaN p-type material) on top of the first semiconductor layer. The P-N interface of semiconductor layers 66 and 65 forms a light-emitting junction 68. The semiconductor layers of LED 62 range in thickness from about 2 to 30 microns, preferably from about 5 to 20 microns, and most preferably from about 8 to 12 microns.

LED 62 has input leads 24 and 26 for applying an electrical potential across P-N junction 68. As shown in FIG. 6, input lead 26 is connected to the anode surface 65 and input lead 24 is connected to the cathode surface 66. In a preferred embodiment, the input lead 24 is connected to the cathode surface 66 of LED 62 at a lower portion of cathode surface 66, as illustrated in FIG. 6. Input lead 24 also may be connected to the cathode surface 66 as described above in connection with FIG. 2. Also in accordance with a preferred embodiment, the input lead 26 is attached to the anode surface 65 of LED 62 by connection pad 63 made of a highly electrically conductive material. Connection pad 63 preferably is made of gold but may be made of other highly electrically conductive materials known to persons skilled in the art. The input lead 26 may be bound to the connection pad 63 by any suitable method including, for example, a ball bond or a wedge bond.

A hole 69 is formed in LED 62 in an orientation generally perpendicular to a plane containing the P-N junction 68. As described above in connection with FIGS. 2–4, the polymer matrix 32 is placed in hole 69 which contains fluorescent indicator molecules whose fluorescence is attenuated or enhanced by the presence of analyte. Because of the extremely small thickness of LED 62 as described above, hole 69 preferably is created by masking a portion of LED 62 and etching hole 69 using techniques known to persons skilled in the art. The masking and etching technique preferably employed to create hole 69 in accordance with this embodiment represents a substantial advantage over the laser ablation technique as described above.

Substrate 64 may be made of any suitable material which is substantially optically transmissive at the wavelength of emission of the indicator molecules. Preferably, substrate 64 may be a material which enables the deposition or fabrication of LED material on its surface. In a preferred embodiment, the substrate 64 is made of a non-conductive, SiC material. The LED 62 and the substrate 64 may be physically joined together by any convenient technique such as, for example, fabrication or deposition.

Figure 8:
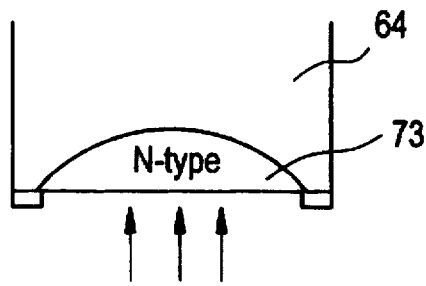
FIGS. 8 and 9 illustrate a photodetector for the sensing device in accordance with an alternative embodiment of the present invention.
Figure 9:
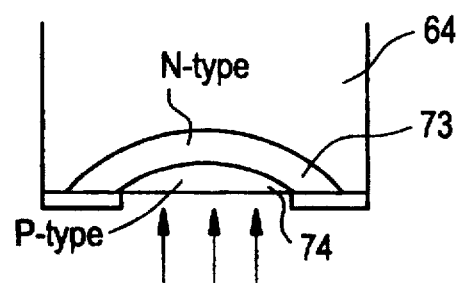

Also in accordance with this embodiment, a photodetector 72 is located at a lower portion of substrate 64 with a photosensitive area below the hole 69, as illustrated in FIG. 6. The photodetector 72 may be a solid state photoelectric device resulting from the interface of two semiconductors. In one embodiment, an N-type semiconductor region 73 and a P-type semiconductor region 74 are formed in substrate 64, as illustrated in FIG. 6. Semiconductor regions 73 and 74 may be formed by techniques known by persons skilled in the art. For example, semiconductor region 73 may be created by masking a portion of the substrate 64 and infusion doping an unmasked region of substrate 64, as illustrated in FIG. 8. The semiconductor region 74 may be created by masking portions of substrate 64 and semiconductor region 73, and infusion doping an unmasked region of semiconductor material 73, as illustrated in FIG. 9. The electrical signal generated by photodetector 72 is transmitted via electrical leads 70 and 71 to appropriate amplification and measuring circuitry (not shown).

Figure 10:
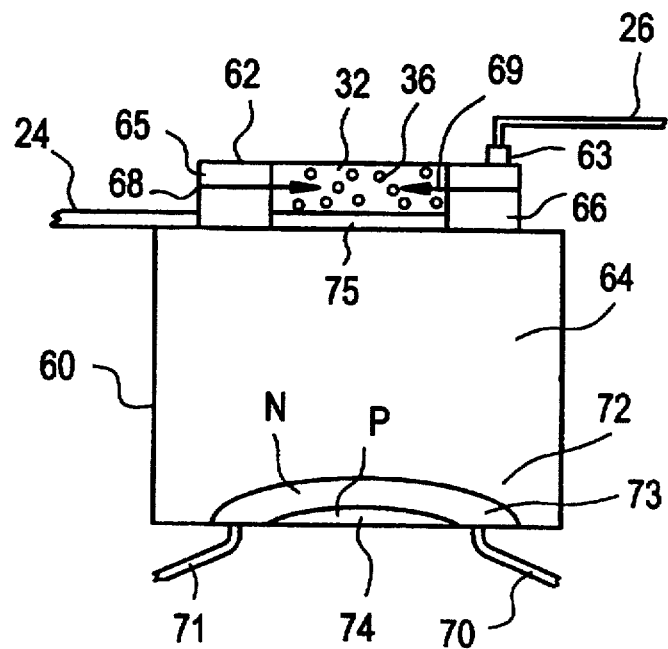
FIG. 10 is a cross-sectional view of another alternative embodiment of a sensing device in accordance with the present invention.

An optical cut-off filter may be interposed between the fluorescent matrix 32 and the photodetector 72. In a preferred embodiment, a filter 75 may be placed in the hole 69 between the fluorescent matrix 32 and the substrate 64, as illustrated in FIG. 10. Filter 75, like filter 41, is designed to transmit fluorescent light emitted from fluorescent indicator molecules 36 while filtering out incident light emitted by LED 62 as well as significant portions of ambient light that would otherwise reach photodetector 23. A preferred filter is a thin-film, dichroic $SiO_2/TiO_2$ electron-beam deposited filter such as those available from Optical Coating laboratories, Inc., Santa Rosa, Calif. U.S.A. and described, for example, in U.S. Pat. No. 5,200,855, incorporated herein by reference. Of course, suitable filters having other formulations as typical also may be used.

As described above in connection with FIGS. 6 and 10, sensor 60 preferably may be a single monolithic structure having an LED region and a detector region. In a preferred embodiment, sensor 60 also may have a filter region.

Figure 11:
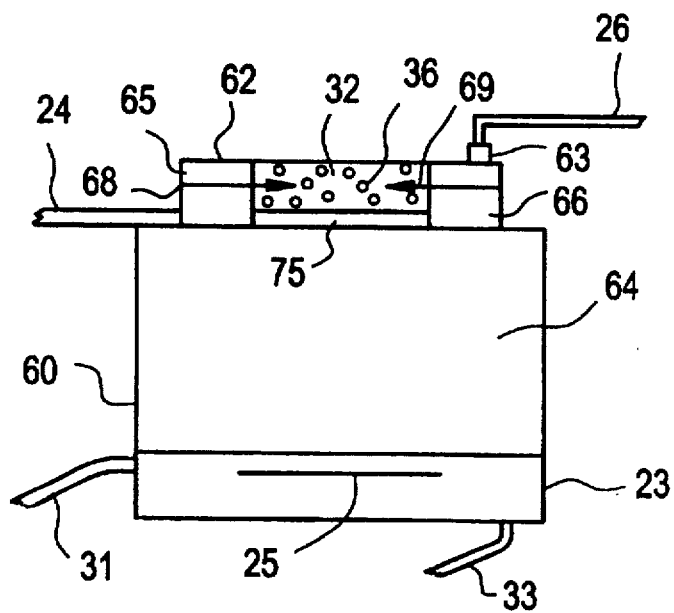
FIG. 11 is a cross-sectional view of another alternative embodiment of a sensing device in accordance with the present invention.

In accordance with yet another embodiment of the invention, a conventional photodetector (such as photodetector 23 described above) may be positioned at one end of the substrate 64 with a photosensitive area 25 below the hole 69, as illustrated in FIG. 11. The photodetector 23 may be connected to the substrate 64 by a suitable optically transmissive adhesive. The electrical signal generated by photodetector 23 is transmitted via electrical leads 31 and 33 to appropriate amplification and measuring circuitry (not shown), as described above. In accordance with this embodiment, sensor 60 also may be provided with an optical cut-off filter as described above. As illustrated FIG. 11, optical cut-off filter 75 may be interposed in hole 69 between the fluorescent matrix 32 and the substrate 64. In an alternative embodiment, an optical cut-off filter may be interposed between the substrate 64 and photodetector 23, as described above in connection with FIGS. 2–4.

Although shown in FIG. 11 as extending from upper and lowers regions of photodetector 23, both electrical leads 31 and 33 may extend from the bottom of photodetector 23. A suitable bottom attach photodetector or "flip chip" as described herein may be obtained by, for example, Advanced Photonics, Camarillo, Calif. The bottom attach photodetector may also be used with the sensor described above in connection with FIGS. 2–5.

The sensors for the present invention are characterized by an extraordinarily small size. For example, the overall dimensions of the sensor are on the order of 200–300 microns on an edge. These sensors also may have overall dimensions as large as about 500 microns and as small as 50 microns on edge. Thus, the sensors may be utilized in micro applications. For example, the sensors are small enough to be implanted under the skin or in a blood vessel. While the sensors have been illustrated in connection with the detection of oxygen concentrations, indicator molecules may be selected that are sensitive to analytes such as glucose, certain hormones, enzymes and the like.

The small volume of fluorescent matrix material and the small photosensitive area of photodetectors 72 and 23 produce devices having a very low dark current. Thus, the signal-to-noise ratio in the devices of this invention are quite good.

Figure 12:
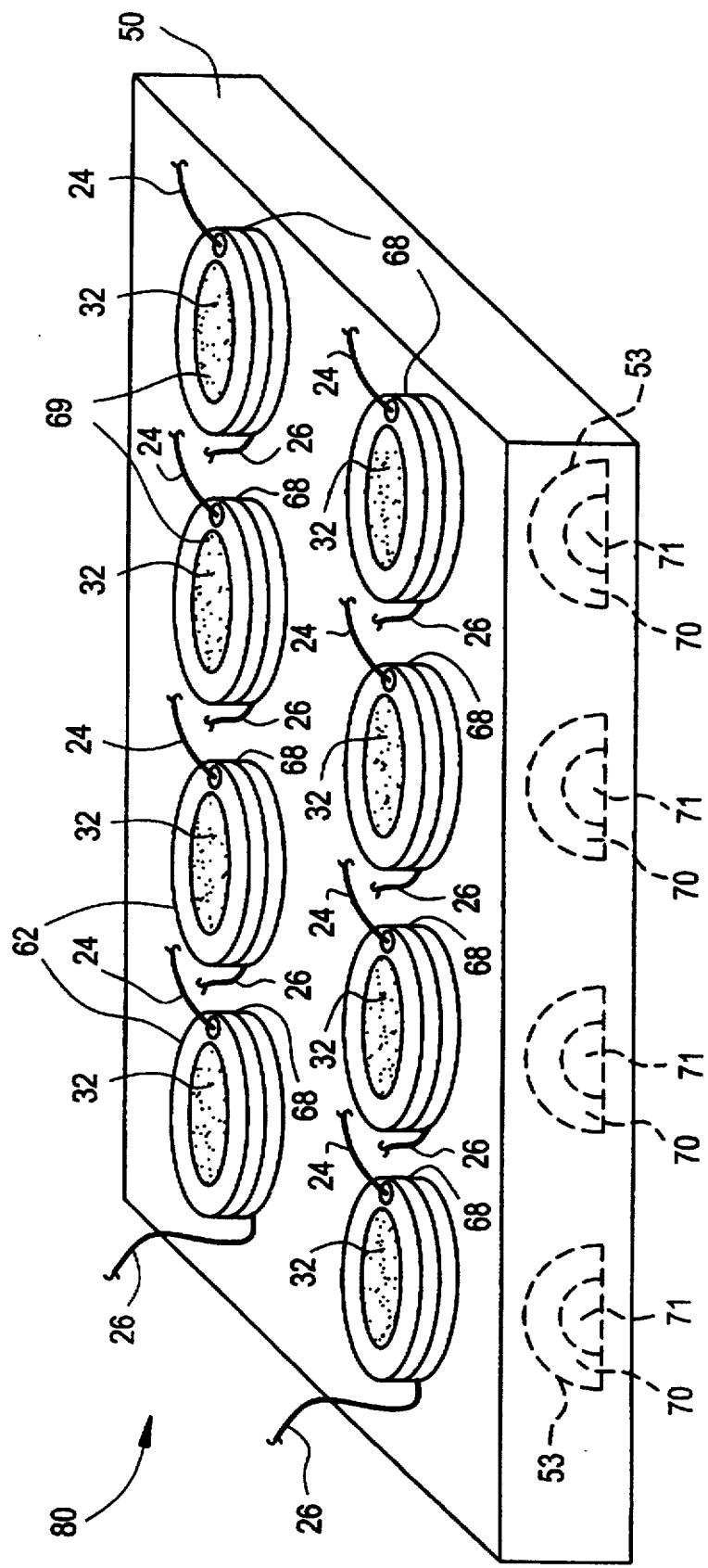
FIG. 12 illustrates a multi-sensor embodiment for simultaneously determining the presence or concentration of a plurality of analytes in a surrounding gaseous or liquid medium.

In view of the extraordinarily small size of the sensors in accordance with the present invention, multiple sensors may be used for simultaneously determining the presence or concentration of a plurality of analytes in a surrounding gaseous or liquid medium. In one embodiment, as illustrated in FIG. 12, a sensor 80 comprises an LED region which may be include a plurality of LEDs 62 and a detector region which may include a plurality of photodetectors 53. LEDs 62 may be formed on substrate 50 by any suitable conventional technique such as, for example, fabrication or deposition. Substrate 50 preferably may be made of a non-conductive, SiC material; however, other suitable substrate materials may be used as known by persons skilled in the art. Each of the LEDs 62 illustrated in FIG. 12 may have essentially the same structure as described above in connection with FIGS. 6, 7 or 10. Preferably, each LED contains a fluorescent matrix 32 which includes a fluorescent indicator molecule 36 whose fluorescence is attenuated or enhanced by a different analyte.

In accordance with this embodiment, photodetectors 53 may be formed on one side of the substrate 50, as illustrated in FIG. 12. Photodetectors 53 preferably include a separate photosensitive area for each LED positioned on substrate 50. Each photosensitive area is positioned such that it receives the fluorescent light emitted from fluorescent indicator molecules 36 in holes 69. In one embodiment, the photodetectors may be formed by masking and infusion doping substrate 50 creating separate P-type and N-type semiconductor regions, as described above in connection with FIGS. 8 and 9. The electrical signals generated by photodetectors 53 are transmitted via electrical leads 70 and 71 to appropriate amplification and measuring circuitry (not shown).

As described above in connection with FIG. 12, sensor 80 preferably may be a single monolithic structure having an LED region and a detector region. In a preferred embodiment, sensor 80 also may have a filter region.

The fluorescent sensors of this invention have been described in connection with certain preferred embodiments. Those skilled in the art will recognize that modifications and improvements may be made without departing from the spirit and scope of the invention as defined by the appended claims.

What is claimed is:

1. A fluorescence sensing device for determining the presence or concentration of an analyte in a liquid or gaseous medium comprises:

(a) a light-emitting diode ("LED") having a semiconductor junction, said LED having an hole oriented generally perpendicular to the semiconductor junction configured such that, upon application of an electrical potential across the junction, light is emitted from said junction into said hole;

(b) an analyte-permeable fluorescent matrix contained within said hole, said fluorescent matrix containing fluorescent indicator molecules whose fluorescence is attenuated or enhanced by the presence of analyte in said fluorescent matrix, said LED and fluorescent indicator molecule being selected such that the wavelength emitted by the LED excites fluorescence in the indicator molecules; and (c) a photodetector at one end of said hole which generates an electrical signal responsive to fluorescent light emitted by said fluorescent indicator molecules.

2. The fluorescence sensing device of claim 1 wherein the fluorescent matrix comprises fluorescent indicator molecules dispersed in a polymer which transmits light at the wavelengths of excitation and emission of the fluorescent indicator molecules.

3. The fluorescence sensing device of claim 1, wherein the longest edge of the LED is less than about 500 microns.

4. The fluorescence sensing device of claim 3, wherein the hole in the LED has a diameter of from about 10 to about 500 microns.

5. The fluorescence sensing device of claim 1, which further comprises a reflective coating on the outer walls of the LED.

6. The fluorescence sensing device of claim 1 or 5, which further comprises an optical cut-off filter interposed between the fluorescence matrix and the photodetector, said optical filter being capable of transmitting light at the wavelength emitted by the fluorescent indicator molecules and absorbing or blocking light at the wavelength emitted by the LED.

7. The fluorescence sensing device of claim 6, wherein said optical cut-off filter is coated on said photodetector.

8. The fluorescence sensing device of claim 6, wherein said optical cut-off filter is placed in said hole between said fluorescent matrix and said photodetector.

9. The fluorescence sensing device of claim 1 or 5, wherein the indicator molecule is the complex, tris(4,7-diphenyl-1,10-phenanthroline)ruthenium(II) perchlorate, and the fluorescence sensing device is an oxygen sensing device.

10. The fluorescence sensing device of claim 1, wherein said LED has a thickness of about 10 to 20 microns.

11. The fluorescence sensing device of claim 1, wherein said sensor comprises a plurality of LEDs each having a hole containing said analyte-permeable fluorescent matrix.

12. The fluorescence sensing device of claim 11, wherein said analyte-permeable fluorescent matrix contained in each of said LEDs contains fluorescent indicator molecules whose fluorescence is attenuated or enhanced by the presence of a different analyte.

13. The fluorescence sensing device of claim 1, wherein said fluorescence sensing device is a single monolithic structure.

14. The fluorescence sensing device of claim 13, wherein said single monolithic structure comprises an LED region and a detector region.

15. The fluorescence sensing device of claim 14, wherein said single monolithic structure further comprises a filter region.

16. The fluorescence sensing device of claim 14, wherein said LED region has a thickness of about 10 to 20 microns.

17. The fluorescence sensing device of claim 1, wherein the longest edge of the LED is less than about 300 microns.

18. A method for determining the presence or concentration of an analyte in a liquid or gaseous medium comprises:

(a) forming a light-emitting diode ("LED") having a semi-conductor junction on a substrate;

(b) forming a hole in said LED oriented generally perpendicular to the semiconductor junction configured such that, upon application of an electrical potential across the junction, light is emitted from said junction into said hole;

(c) placing an analyte-permeable fluorescent matrix within said hole, said fluorescent matrix containing fluorescent indicator molecules whose fluorescence is attenuated or enhanced by the presence of analyte in said fluorescent matrix, selecting said LED and fluorescent indicator molecule such that the wavelength emitted by the LED excites fluorescence in the indicator molecules; and (d) forming a photodetector at one end of said substrate which generates an electrical signal responsive to fluorescent light emitted by said fluorescent indicator molecules.

19. The method of determining the presence or concentration of an analyte in a liquid or gaseous medium of claim 18, further comprising fabricating said fluorescence sensing device as a single monolithic structure.

20. The method of determining the presence or concentration of an analyte in a liquid or gaseous medium of claim 18, wherein the step of forming the hole in said LED further comprises etching a hole in said LED.

21. The method of determining the presence or concentration of an analyte in a liquid or gaseous medium of claim 18, wherein the step of forming an LED on the substrate further comprises forming an LED on a substrate made of SiC.

* * * * *

UNITED STATES PATENT AND TRADEMARK OFFICE
CERTIFICATE OF CORRECTION

PATENT NO. : 5,894,351
DATED : April 13, 1999
INVENTOR(S) : Arthur E. Colvin, Jr.

It is certified that error appears in the above-identified patent and that said Letters Patent is hereby corrected as shown below:

In the Specification:
Column 4,
Line 36, after "lead" insert -- 26 --;
Line 56, "FIGS." should be -- FIG. --;

In the Claims:
Column 7,
Line 61, "an" should be -- a --.

Signed and Sealed this

Twenty-sixth Day of June, 2001

*Attest:*

*Attesting Officer*

NICHOLAS P. GODICI
*Acting Director of the United States Patent and Trademark Office*